United States Patent [19]
Martin et al.

[11] Patent Number: 4,482,547
[45] Date of Patent: Nov. 13, 1984

[54] SUBSTITUTED-1,3,4-BENZOTRIAZEPINES

[75] Inventors: Lawrence L. Martin, Lebanon; Linda L. Setescak, Somerville, both of N.J.

[73] Assignee: Hoechst-Roussel Pharmaceuticals Inc., Sommerville, N.J.

[21] Appl. No.: 412,047

[22] Filed: Aug. 26, 1982

[51] Int. Cl.³ .................... A61K 31/55; C07D 255/04
[52] U.S. Cl. ......................... 424/244; 260/239 BD; 260/239.3 B; 548/546; 560/21; 560/34; 564/151; 564/310; 564/313
[58] Field of Search ................. 260/239 BD; 424/244

[56] References Cited

U.S. PATENT DOCUMENTS 3,176,008  3/1965  Sulkowski et al. .......... 260/239 BD
4,309,424  1/1982  Martin et al. ............... 260/239 BD

OTHER PUBLICATIONS

Paal et al., Ber. Deut. Chem., vol. 25, pp. 2896–2904 (1892).
Kadin, J. Org. Chem., vol. 38, pp. 1348–1350 (1973).
Geyer, III et al., J. Med. Chem., vol. 25, pp. 340–346 (1982).
Fusco et al., Tetrahedron Letters, vol. 23, No. 17, pp. 1829–1830 (1982).

Primary Examiner—Alton D. Rollins

Attorney, Agent, or Firm—James R. Cartiglia

[57] ABSTRACT

This invention relates to substituted-1,3,4-benzotriazepines of the formula

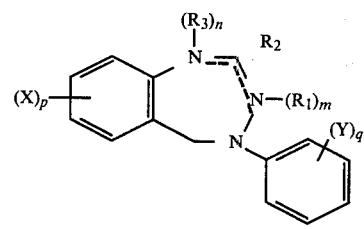

wherein X and Y are each independently hydrogen, lower alkyl, halogen, lower alkoxy, nitro and hydroxyl; $R_1$ and $R_3$ are each independently hydrogen or alkyl; $R_2$ is hydrogen, lower alkyl, cycloalkyl lower alkyl, phenyl, Ar lower alkyl, hydroxyl and sulfhydryl; m and n are each independently integers of 0 or 1 and when m is 0, n is 1 and vice-versa; and p and q are independently integers of 1 or 2. Also included in the invention are the substituted-1,3,4-benzotriazepine derivatives of tautomeric form when the substituent for $R_1$ and/or $R_3$ in the above formula is hydrogen. The compound of this invention may be used as antihypertensive agents.

25 Claims, No Drawings

SUBSTITUTED-1,3,4-BENZOTRIAZEPINES

To the best of our knowledge the compounds of the present invention have not heretofore been described or suggested.

The compounds of the present invention have the general formula

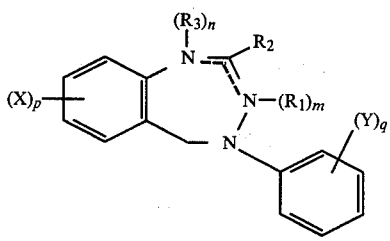
(I)

wherein X and Y are each independently hydrogen, lower alkyl, halogen, lower alkoxy, nitro and hydroxyl; $R_1$ and $R_3$ are each independently hydrogen or lower alkyl; $R_2$ is hydrogen, lower alkyl, cycloalkyl lower alkyl, phenyl, Ar lower alkyl, hydroxyl and sulfhydryl; m and n are each independently integers of 0 or 1 and when m is 0, n is 1 and vice-versa; p and q are each independently integers of 1 or 2; and wherein when the substituent for $R_1$ and/or $R_3$ is hydrogen and $R_2$ is not hydroxyl or sulfhydryl the 1,3,4-benzotriazepine is of the tautomeric formulae

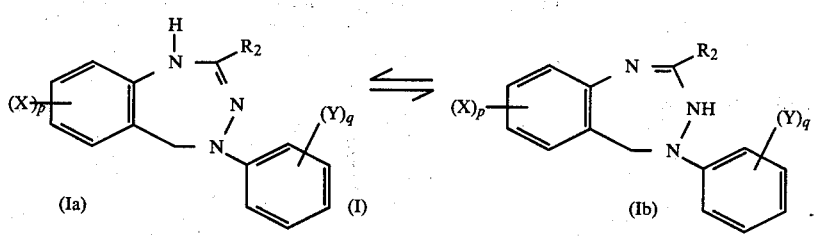
(Ia)    (I)    (Ib)

When $R_2$ is hydroxyl or sulfhydryl and $R_1$ and/or $R_3$ is hydrogen the 1,3,4-benzotriazepine is of the tautomeric formulae

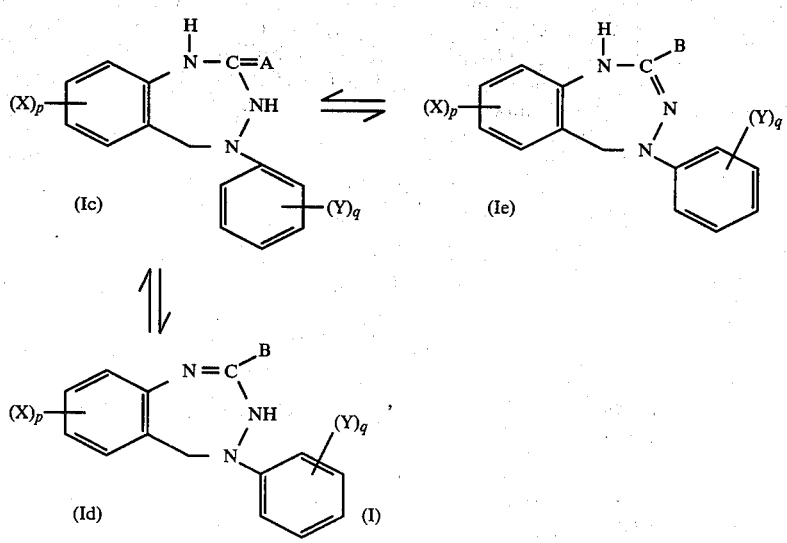
(Ic)    (Ie)
(Id)    (I)

wherein A is O or S and B is OH or SH.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc; the term "phenyl" includes unsubstituted and substituted phenyl groups, e.g.

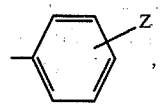

p-nitrophenyl, o-toluyl, m-methoxyphenyl, etc; the term "Ar lower alkyl" refers to a monovalent substituent which consists of a substituted or unsubstituted phenyl group linked through a lower alkylene group having its free valence bond from a carbon of the lower alkylene group, and having a formula

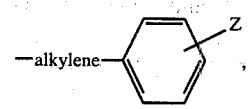

where Z is hydrogen, halogen, lower alkyl, lower alkoxy, $CF_3$, $NO_2$ and $NH_2$; the term "alkylene" refers to a bivalent radical of the lower branched or unbranched alkyl group it is derived from having valence bonds from two terminal carbons thereof, e.g. ethylene (—CH$_2$CH$_2$—), propylene (—CH$_2$CH$_2$CH$_2$—), isopropylene

etc.; the term "cycloalkyl lower alkyl" refers to a monovalent substituent consisting of a saturated hydrocarbon group possessing at least one carbocyclic ring, of 3 to 7 carbon atoms, e.g., cyclopropyl, cyclobutyl, cyclopentyl, cyclohexyl, cycloheptyl, linked through a lower alkyl group; and the term "halogen" refers to a member of the family consisting of fluorine, chlorine, bromine and iodine.

Preferred compounds of the invention are those where R$_2$ is lower alkyl or hydroxyl and R$_1$ and/or R$_3$ is hydrogen. Most preferred of these preferred compounds are those where R$_2$ is a straight or branched chain propyl or butyl.

The compounds of the invention are prepared in the following manner. The substituents X, Y, R$_1$, R$_2$, R$_3$ and the integers m, n p and q are as defined above unless indicated otherwise.

A phenyl hydrazine of the formula

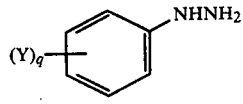

is selected. Compound II is reacted with a 2-nitrobenzyl halide of the formula

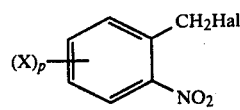

where Hal is a halogen, under conventional substitution reaction conditions, typically in the presence of a polar solvent, e.g. ethanol, at a temperature of 25° C. to reflux of solvent employed for 1 to 24 hours to form Compound IV having the formula

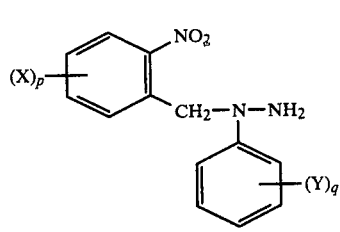

Compound IV is reduced in a conventional manner, as for example with iron and hydrochloric acid or in the manner described by C. Paal and A. Bodewig, Berichte 25, 2896 (1892). Typically, Compound IV is combined with iron and hydrochloric acid in the presence of alcohol at a temperature ranging from 25° C. to reflux for about 0.1 to 6 hours to form an amino hydrazine of the formula

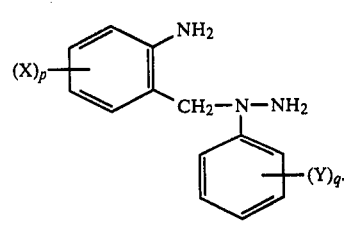

To prepare Compound VI of the formula

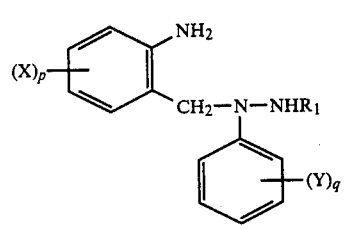

where R$_1$ is lower alkyl, Compound IV is acylated in a conventional manner with a conventional acylating agent, such as

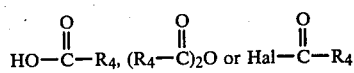

where Hal is a halogen and R$_4$ is hydrogen, an alkyl of 1 to 5 carbon atoms, a C$_1$–C$_5$ alkoxy or phenoxy to form a compound having the formula

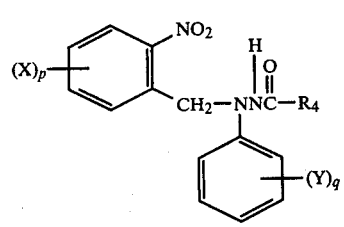

Compound VII in turn is conventionally reduced by a reducing agent compatible with the phenyl nitro group, e.g. diborane, borane-methylsulfide complex, etc., as for example described in U.S. Pat. No. 4,309,424 to form Compound VIII of the formula

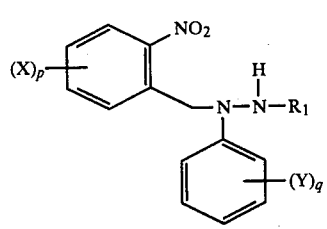

Compound VIII is then reduced with iron and hydrochloric acid, as described above to form Compound VI.

Compound V or Compound VI is cyclized as described in U.S. Pat. No. 4,309,424, incorporated hereinto by reference with a compound of the formula R$_2$—C—(O—lower alkyl)$_3$ to provide the corresponding 1,3,4-benzotriazepine of Compound I. This cyclization is carried out in the presence of an acid catalyst such as hydrochloric acid at a temperature of from 25° C. to reflux. As indicated above, where Compound V is cyclized, i.e. where $R_1$ and/or $R_3$ is hydrogen, a tautomeric form or system exists, namely

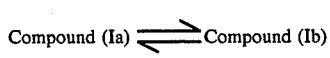

Compound (I)

In an alternative procedure, Compound V or Compound VI is reacted with carbon disulfide at a temperature of 25° to 100° C. for 1 to 48 hours to form a thione of the formula

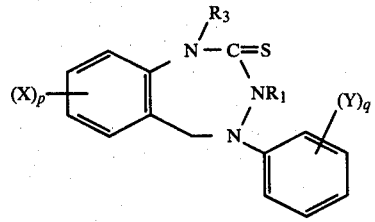

where $R_1$ is hydrogen or lower alkyl and $R_3$ is hydrogen, or its respective tautomers

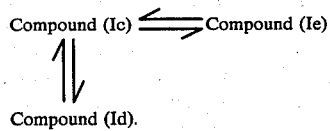

[Compound I]

In the alternative procedure, Compound V or Compound VI is reacted with 1,1'-carbonyl diimidazole in an aprotic solvent, such as tetrahydrofuran, at a temperature of 5° C. to reflux for 0.1 to 48 hours to form a keto compound of the formula

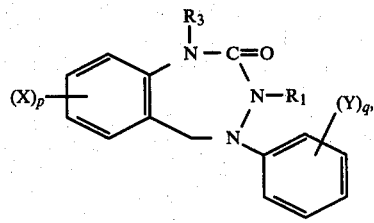

where $R_1$ is hydrogen or lower alkyl and $R_3$ is hydrogen or its respective tautomers,

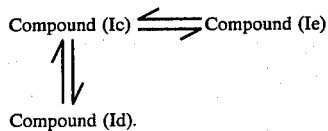

To obtain Compound I where $R_3$ is lower alkyl, compound VII is reduced, as previously described, by reaction with iron and hydrochloric acid to form Compound XI of the formula

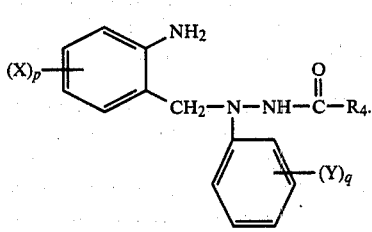

Compound XI is reacted with an aldehyde having the formula

where $R_5$ is hydrogen or $(C_1-C_5)$ alkyl e.g.

in the presence or absence of succinimide to form compounds of the formula

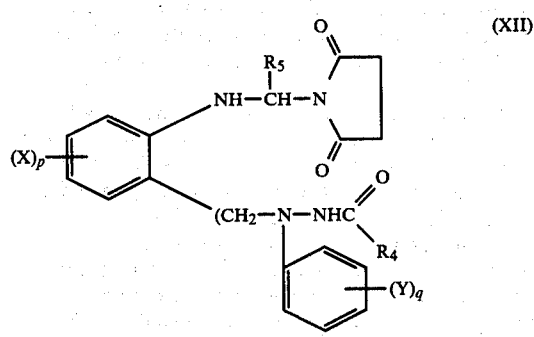

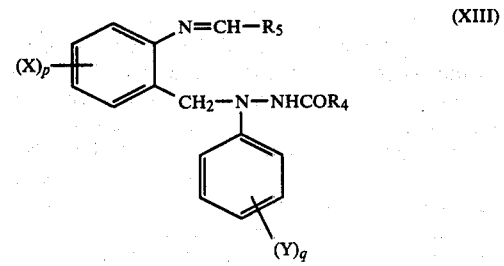

Compounds XII or XIII are reduced with a borohydride, for example sodium borohydride, in an appropriate solvent such as dimethylsulfoxide (DMSO), ethanol, etc. to afford compound XIV.

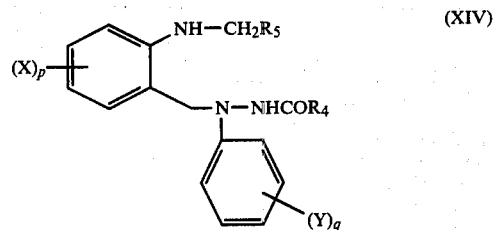

In the case of XII, DMSO is preferred.

The synthesis of XII and XIII generally follow the teachings in the art such as those described by S. B. Kadin, J. Organic Chemistry, 38, 1348 (1973) and L. L. Martin & L. L. Setescak et al., J. Medicinal Chemistry, 25, 340 (1982).

Compound XIV is then cyclized in a conventional manner by treatment with a conventional dehydrating agent, such as $PCl_5$, $POCl_3$, thionyl chloride, etc. in a solvent such as $CHCl_3$, etc. at a temperature ranging from ambient temperature to the reflux temperature of the reaction mixture for 1 to 24 hours to form a compound of the invention having the formula I, where $R_3$ is lower alkyl and n=1.

Alternatively, compound XIV can be hydrolyzed to provide a compound XV having the formula

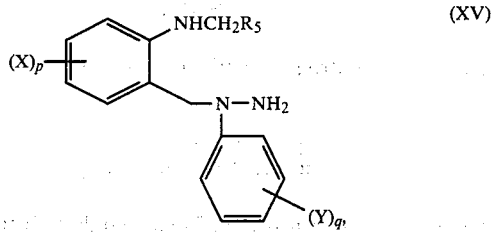

which can be cyclized to a compound of formula I wherein $R_3$ is lower alkyl and n is 1. The hydrolysis can be effected under alkaline or acidic conditions. The cyclization can be carried out as described in U.S. Pat. No. 4,309,424.

Alternatively, compounds of formula I wherein either $R_3$ is lower alkyl and n=1 or $R_1$ is lower alkyl and m=1 can be provided by direct alkylation of a compound of formula I wherein $R_3$ is hydrogen and n=1 or $R_1$ is hydrogen and m=1. Such alkylation can be effected for example by treating the latter compound with n-butyl lithium followed by an alkyl p-toluene sulfonate. Normally a mixture of both products are formed (compound I, $R_3$=alkyl; compound I, $R_1$=alkyl) which can be readily separated by conventional techniques such as column chromatography.

The 1,3,4-benzotriazepines of the invention are useful as antihypertensive agents due to their ability to depress blood pressure in mammals. Antihypertensive activity is measured in the spontaneous hypertensive rat by the indirect tail cuff method described in "Methods in Pharmacology," A. Schwartz, Ed., Vol. I, Appleton-Century Crofts, New York, 1971, p. 135. In this procedure a group of five animals are treated orally (p.o.) for three days with the test compound in relation to the control group of the same number. The drop in blood pressure is measured on the third day by following administration. The antihypertensive activities of some of the compounds, expressed as mm decrease in mean arterial blood pressure are given in Table I.

TABLE I

| Compound | Dose (p.o.) mg/kg of body weight | Decrease in Blood Pressure mm/Hg |
| --- | --- | --- |
| 4,5-dihydro-2-ethyl-4-phenyl-3H—1,3,4,-benzo-triazepine hydrochloride | 50 | 34 |
| 4,5-dihydro-4-phenyl-2-(n-propyl)-3H—1,3,4-benzo-triazepine hydrochloride | 50 | 54 |
| 4,5-dihydro-4-phenyl-2-(n-butyl)-3H—1,3,4-benzo-triazepine hydrochloride | 50 | 48 |

TABLE I-continued

| Compound | Dose (p.o.) mg/kg of body weight | Decrease in Blood Pressure mm/Hg |
| --- | --- | --- |
| 4,5-dihydro-4-phenyl-2-(isopropyl)-3H—1,3,4-benzotriazepine hydrochloride | 50 | 43 |
| 1,3,4,5-tetrahydro-4-phenyl-2H—1,3,4-benzotriazepine-2-one | 50 | 35 |

Blood pressure reduction is achieved when the compounds of the invention are administered to a subject requiring such treatment at an effective oral, parenteral or intravenous dose of from 0.1 to 50 mg/kg of body weight per day. A preferred effective dose within this range is from about 0.1 to 5 mg/kg of body weight per day. A particularly preferred effective amount is about 1 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purposes of oral therapeutic administrtion, the compounds may be incorporated with excipients and used in the form of tablets, troches, capsules, elixirs, suspensions, syrups, wafers, chewing gums and the like. These preparations should contain at least 4% of the 1,3,4-benzotriazepines of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0-300 milligrams of the 1,3,4-benzotriazepines of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 1,3,4-benzotriazepines of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the 1,3,4-benzotriazepines of the invention.

The solutions or suspensions may also include the following adjuvants: a sterile diluent such as water for injection, saline solution, fixed oils, polyethylene glycols, glycerin, propylene glycol or other synthetic solvent; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Other compounds of the invention include:
4,5-dihydro-4-(3-methylphenyl)-3H-1,3,4-benzotriazepine;
4,5-dihydro-4-(3-nitrophenyl)-3H-1,3,4-benzotriazepine;
4,5-dihydro-4-(4-hydroxyphenyl)-3H-1,3,4-benzotriazepine;
4,5-dihydro-4-(3-propoxyphenyl)-3H-1,3,4-benzotriazepine;
4,5-dihydro-2-hydroxyl-4-phenyl-3H-1,3,4-benzotriazepine;
4,5-dihydro-2-sulfhydryl-4-phenyl-3H-1,3,4-benzotriazepine;
4,5-dihydro-3-n-butyl-2-methyl-3H-1,3,4-benzotriazepine;
4,5-dihydro-7-ethyl-4-phenyl-3H-1,3,4-benzotriazepine;
4,5-dihydro-8-bromo-2-n-butyl-4-phenyl-3H-1,3,4-benzotriazepine;
4,5-dihydro-8-hydroxy-4-phenyl-3H-1,3,4-benzotriazepine;
4,5-dihydro-7-nitro-4-phenyl-3H-1,3,4-benzotriazepine;
4,5-dihydro-7-methoxy-4-phenyl-2-n-propyl-3H-1,3,4-benzotriazepine;
4,5-dihydro-1-methyl-4-phenyl-1H-1,3,4-benzotriazepine; and
4,5-dihydro-7-chloro-4-phenyl-3H-1,3,4-benzotriazepine.

The following examples are for illustrative purposes and are not to be construed as limiting the invention disclosed herein. All temperatures are given in degrees centigrade.

EXAMPLE 1 a. 1-[(2-nitrophenyl)methyl]-1-phenylhydrazine

To a solution of 21.6 g (0.2 m) of phenylhydrazine in 50 ml of absolute ethanol, a slurry of 17.2 g (0.1 m) of o-nitrobenzyl chloride in 30 ml of absolute ethanol was added at room temperature. The mixture was refluxed (steam bath) for 3.5 hours. The mixture turned red and a precipitate formed. The reaction mixture was poured into 1 liter of hot buffer (0.1 m sodium acetate and 0.1 m acetic acid in 1 liter $H_2O$; pH=5). A red oil formed which was, after decanting the aqueous phase, extracted with ether, and the ethereal phase was washed with water, dried ($Na_2SO_4$) and filtered. Ethereal HCl was added dropwise and the product precipitated as the hydrochloride salt. The salt was rinsed thoroughly with ether and dried to give 21.4 g (76%) of crystalline material, m.p. 290°–294° C. The free base was liberated by partitioning between dilute NaOH and ether to give after concentration of the ethereal phase, a red solid which was recrystallized from ethanol to give 1-[(2-nitrophenyl)methyl]-1-phenylhydrazine, m.p. 67°–69° C.

ANALYSIS:
Calculated for $C_{13}H_{13}N_3O_2$: 64.19%C; 5.38%H; 17.27%N; Found: 64.16%C; 5.22%H; 17.23%N.

b. 4,5-Dihydro-2-methyl-4-phenyl-3H-1,3,4-benzotriazepine hydrochloride

To a solution of 25 g (0.12 m) of 1-[(2-nitrophenyl)methyl]-1-phenylhydrazine of Example 1a in 300 ml of 95% ethanol and 75 ml of $H_2O$, 67 g (1.2 g-atom) of iron (reduced electrolytic) was added followed by the addition of 2 ml of concentrated HCl. The mixture was refluxed 0.5 hour to reduce the nitro group to form an amino hydrazine thereof. Celite was added and the reaction mixture was filtered. The filter cake was rinsed with additional 95% ethanol. The filtrate was evaporated. The residual material was basified with 10% NaOH and extracted with ether. The ether was washed with water, dried ($Na_2SO_4$), filtered and evaporated giving 20 g of the resulting aminohydrazine, 1-[(2-aminophenyl)methyl]-1-phenylhydrazine, as a solid. A mixture of 2.5 g (0.012 m) of the resulting aminohydrazine, 11.68 g (0.072 m) of triethylorthoacetate, and 4.5 ml of acetic acid was refluxed 3.5 hours. The solvents were evaporated. The residue was partitioned between 10% NaOH and ether. The ether extract was washed with water, dried ($Na_2SO_4$) and filtered. Ethereal HCl was added to the filtrate and the product precipitated as the hydrochloride salt, 3.28 g (91%). Recrystallization from absolute ethanol-ether gave 2 g of 4,5-dihydro-2-methyl-4-phenyl-3H-1,3,4-benzotriazepine hydrochloride, m.p. 244°–247° C.

ANALYSIS:
Calculated for $C_{15}H_{15}N_3.HCl$: 65.82%C; 5.90%H; 15.37%N; Found: 66.13%C; 5.92%H; 15.15%N.

EXAMPLE 2

4,5-Dihydro-2-ethyl-4-phenyl-3H-1,3,4-benzotriazepine hydrochloride

A mixture of 3.75 g (0.018 m) of the aminohydrazine of Example 1b, 19.04 g (0.108 m) of triethyl orthopropionate, and 6.75 ml acetic acid was refluxed 3 hours. The solvents were evaporated. The residue was partitioned between 10% NaOH and ether. The ether extract was washed with water, dried ($Na_2SO_4$) and filtered. Ethereal-HCl was added to the filtrate and the product precipitated as the hydrochloride salt (4.75 g). Recrystallization from absolute ethanol gave 2 g (40%) of 4,5-dihydro-2-ethyl-4-phenyl-3H-1,3,4-benzotriazepine hydrochloride, m.p. 236°–239° C.

ANALYSIS:

Calculated for $C_{16}H_{17}N_3 \cdot HCl$: 66.78%C; 6.30%H; 14.60%N; Found: 66.46%C; 6.39%H; 14.26%N.

EXAMPLE 3

4,5-Dihydro-4-phenyl-2-(n-propyl)-3H-1,3,4-benzotriazepine hydrochloride

A mixture of 4.26 g (0.019 m) of the amino hydrazine of Example 1b, 17.8 g (0.12 m) of trimethyl orthobutyrate and 7.5 ml of acetic acid was refluxed 3 hours. After standing overnight (about 16 hours) the solution was evaporated and the residue was partitioned between 10% NaOH and ether. The ether extract was dried ($Na_2SO_4$) and filtered. Ethereal HCl was added to the filtrate and the product precipitated as the HCl salt. The precipitate was triturated with hot acetonitrile giving 3.2 g (56%) of 4,5-dihydro-4-phenyl-2-(n-propyl)-3H-1,3,4-benzotriazepine hydrochloride, m.p. 190°–195° C.

ANALYSIS:

Calculated for $C_{17}H_{19}H_3 \cdot HCl$: 67.65%C; 6.34%H; 13.92%N; Found: 68.05%C; 6.63%H; 13.92%N.

EXAMPLE 4

4,5-Dihydro-2,4-diphenyl-3H-1,3,4-benzotriazepine hydrochloride

A mixture of 4.26 g (0.02 m) of the aminohydrazine of Example 1b, 21 g (0.12 m) of trimethyl orthobenzoate, and 7.5 ml of acetic acid was refluxed 3 hours. The solvents were evaporated. The residue was partitioned between 10% NaOH and ether. The ether extract was washed with water, dried ($Na_2SO_4$) and filtered. Ethereal-HCl was added to the filtrate and the product precipitated as the hydrochloride salt. The crude material was triturated with isopropanol giving 3.1 g (46%) of 4,5-dihydro-2,4-diphenyl-3H-1,3,4-benzotriazepine hydrochloride, m.p. 205°–208° C.

ANALYSIS:

Calculated for $C_{20}H_{17}N_3 \cdot HCl$: 71.53%C; 5.10%H; 12.51%N; Found: 71.44%C; 5.38%H; 12.32%N.

EXAMPLE 5

4,5-Dihydro-4-phenyl-2-(n-butyl)-3H-1,3,4-benzotriazepine hydrochloride

To a slightly warmed solution (40° C.) of 3 g (0.014 m) of the aminohydrazine of Example 1b in 40 ml of acetonitrile and 5.7 g (0.028 m) of triethyl orthopentanoate, ethereal HCl was added until the solution was acidic. The mixture was brought to a gentle reflux and after a few minutes a precipitate began to form. The mixture was refluxed overnight (about 16 hours). The reaction mixture was cooled and the product filtered off. The filter cake was washed thoroughly with ether to give 4 g (90%) of 4,5-dihydro-4-phenyl-2-(n-butyl)-3H-1,3,4-benzotriazepine hydrochloride, m.p. 211°–213.5° C.

ANALYSIS:

Calculated for $C_{18}H_{21}H_3 \cdot HCl$: 68.45%C; 7.02%H; 13.30%N; Found: 68.43%C; 7.11%H; 13.45%N.

EXAMPLE 6

4,5-Dihydro-4-phenyl-2-(isopropyl)-3H-1,3,4-benzotriazepine hydrochloride

A mixture of 3 g (0.014 m) of the aminohydrazine of Example 1b and 5.7 g (0.028 m) of triethyl orthoisobutyrate and 40 ml of acetonitrile was warmed in a 40° C. oil bath. Sufficient ethereal HCl was added to make the solution acidic and, after 10 minutes, a precipitate formed. The mixture was refluxed overnight. The mixture was cooled and filtered to give 2.8 g of product. Recrystallization from methanol-ether afforded 2.14 g (51%) of 4,5-dihydro-4-phenyl-2-(isopropyl)-3H-1,3,4-benzotriazepine hydrochloride, m.p. 245°–248° C.

ANALYSIS:

Calculated for $C_{17}H_{19}N_3 \cdot HCl$: 67.65%C; 6.67%H; 13.92%N; Found: 67.79%C; 6.65%H; 13.92%N.

EXAMPLE 7

1,3,4,5-Tetrahydro-4-phenyl-2H-1,3,4-benzotriazepin-2-thione

A mixture of 4 g (0.019 m) of the aminohydrazine of Example 1b and 1.6 g (0.02 m) of $CS_2$ in 40 ml of 95% ethanol was placed in a 35° C. oil bath, warmed to 60°–64° C. and held 1 hour at that temperature. Concentrated hydrochloric acid (1 ml) was added and the mixture was refluxed overnight. The product began to crystallize and ether was added to further enhance crystallization. The mixture was cooled and the precipitate was filtered giving 3.6 g (74%) of product. The resultant product was triturated with warm 95% ethanol to give 1,3,4,5-tetrahydro-4-phenyl-2H-1,3,4-benzotriazepin-2-thione, m.p. 242°–244° C.

ANALYSIS:

Calculated for $C_{14}H_{13}N_3S$: 65.86%C; 5.13%H; Found: 66.10%C; 5.32%H.

EXAMPLE 8

1,3,4,5-Tetrahydro-4-phenyl-2H-1,3,4-benzotriazepine-2-one

A stirred, chilled suspension of 15 g (0.07 m) of the aminohydrazine of Example 1b in 250 ml of tetrahydrofuran was treated with 17 g (0.105 m) of 1,1'-carbonyldiimidazole in 350 ml of tetrahydrofuran over 30 minutes. The mixture was refluxed for two days. The solvents were evaporated, and the residue was triturated with 5% HCl, filtered, and rinsed with water and then acetone to give 13.25 g (80%) of 1,3,4,5-tetrahydro-4-phenyl-2H-1,3,4-benzotriazepine-2-one, m.p. 283°–286° C.

ANALYSIS:

Calculated for $C_{14}H_{13}N_3O$: 70.28%C; 5.47%H; 17.56%N. Found: 70.36%C; 5.59%H; 17.40%N.

EXAMPLE 9 a.
2-Formyl-1-[(2-nitrophenyl)methyl]-1-phenylhydrazine

A stirred solution of 48.66 g (0.2 mol) of 1-[(2-nitrophenyl)methyl]-1-phenylhydrazine and 200 ml of 97% formic acid solution was heated 4 hours under reflux and allowed to stand overnight (about 16 hours) at ambient temperature. Excess formic acid was removed on a rotary evaporator and the residue was dissolved in 1500 ml of $CH_2Cl_2$. The solution was washed with 10% NaOH and concentrated to dryness. Recrystallization from 600 ml of 95% ethanol afforded 44.0 g (81.8%) of 2-formyl-1-[(2-nitrophenyl)methyl]-1-phenylhydrazine, m.p. 140°–142.5° C.

b.
2-Methyl-1-[(2-nitrophenyl)methyl]-1-phenylhydrazine hydrochloride

To a solution of 30 g (0.11 mol) of 2-formyl-1-[(2-nitrophenyl)methyl]-1-phenylhydrazine of Example 9a and 1000 ml of sieve dried tetrahydrofuran (THF), 333 ml of borane-methyl sulfide complex (1M solution in $CH_2Cl_2$) was added dropwise and at such a rate that the temperature did not exceed 25° C. The mixture was stirred overnight at ambient temperature. Ethereal HCl was added to hydrolyze the complex. The reaction mixture was then basified with 10% NaOH. The tetrahydrofuran was evaporated and the residue was extracted with ether. The ether extract was washed, dried ($Na_2SO_4$), filtered and evaporated to give 28 g of an oil as a mixture of products. The mixture was separated by high pressure liquid chromatography (HPLC)(toluene, silica gel column, 250 ml/min.) The product was isolated as a solid, 20 g (71%). The solid was dissolved in absolute ethanol, ethereal-HCl was added and the product, 2-methyl-1-[(2-nitrophenyl)methyl]-1-phenylhydrazine hydrochloride, crystallized as the hydrochloride salt, m.p. 169°–172° C.

ANALYSIS:

Calculated for $C_{14}H_{15}N_3O_2 \cdot HCl$: 57.24%C; 5.49%H; 14.30%N; Found: 57.01%C; 5.12%H; 14.02%N.

c.
1-[(2-aminophenyl)methyl]-2-methyl-1-phenylhydrazine

A mixture of 30.8 g (0.12 m) of 2-methyl-1-[(2-nitrophenyl)methyl]-1-phenylhydrazine of Example 9b, 67 g (1.2 m) of iron and 3 ml of concentrated HCl in 360 ml of 95% ethanol and 90 ml of water was refluxed 30 minutes. To the cooled mixture, Celite was added and the mixture was filtered. The filtrate was evaporated and the residue was partitioned between 10% NaOH and ether. The ether extract was washed with water, dried ($Na_2SO_4$), filtered and evaporated to give 25 g of an oil. Trituration with isopropyl ether and hexane gave a solid. Recrystallization from isopropanol-hexane gave 15.7 g (58%) of 1-[(2-aminophenyl)methyl]-2-methyl-1-phenylhydrazine, m.p. 57°–59° C.

ANALYSIS:

Calculated for $C_{14}H_{17}N_3$: 73.98%C; 7.54%H; 18.48%N; Found: 74.06%C; 7.46%H; 18.56%N.

d.
4,5-Dihydro-2,3-dimethyl-4-phenyl-3H-1,3,4-benzotriazepine hydrochloride

To a solution of 3.5 g (0.0154 m) of 1-[(2-aminophenyl)methyl]-2-methyl-1-phenylhydrazine of Example 9c in 40 ml of acetonitrile and 4.87 g (0.03 m) of triethyl orthoacetate was added sufficient ethereal HCl to make the solution acidic. The mixture was refluxed 5.5 hours. The solvents were evaporated and the residue was partitioned between 10% NaOH and ether. The ether extract was washed with water, dried ($Na_2SO_4$) and filtered. The product was precipitated with ethereal HCl to afford 2.63 g (60%) of 4,5-dihydro-2,3-dimethyl-4-phenyl-3H-1,3,4-benzotriazepine hydrochloride, m.p. 274°–277° C.

ANALYSIS:

Calculated for $C_{16}H_{17}N_3 \cdot HCl$: 66.78%C; 6.30%H; 14.60%N; Found: 66.90%C; 6.33%H; 14.40%N.

EXAMPLE 10

4,5-Dihydro-2-ethyl-3-methyl-4-phenyl-3H-1,3,4-benzotriazepine hydrochloride

To a mixture of 3.5 g (0.0154 m) of 1-[(2-aminophenyl)methyl]-2-methyl-1-phenylhydrazine of Example 9c and 5.43 g of triethyl orthopropionate in 40 ml of acetonitrile, sufficient ethereal HCl was added to make the solution acidic. The mixture was refluxed 8 hours and the solvent was evaporated. The residue was partitioned between 10% NaOH and ether. The ether extract was washed with water, dried ($Na_2SO_4$) and filtered. Ethereal HCl was added to the filtrate and the precipitate was collected and dried to give 4,5-dihydro-2-ethyl-3-methyl-4-phenyl-3H-1,3,4-benzotriazepine hydrochloride, 2.0 g (43%), m.p. 126°–130° C.

ANALYSIS:

Calculated for $C_{17}H_{19}N_3 \cdot HCl$: 67.65%C; 6.68%H; 13.92%N; Found: 67.79%C; 6.66%H; 13.55%N.

EXAMPLE 11

4,5-Dihydro-3-methyl-4-phenyl-2-n-propyl-3H-1,3,4-benzotriazepine

To a solution of 2.37 g (0.01 m) of 1-[(2-aminophenyl)methyl]-2-methyl-1-phenylhydrazine of Example 9c in 40 ml of acetonitrile and 2.96 g (0.02 m) of trimethyl orthobutyrate, enough ethereal HCl was added to make the solution acidic. The mixture was warmed at 50° C. for 2.5 hours and then refluxed for 3.5 hours. The solvent was evaporated and the residue partitioned between 10% NaOH and ether. The ether solution was extracted with 5% HCl. The aqueous acidic solution was basified with 10% NaOH and the product was extracted with ether. The ether extract was dried ($Na_2SO_4$), filtered and evaporated to give 2.8 g (93%) of 4,5-dihydro-3-methyl-4-phenyl-2-n-propyl-3H-1,3,4-benzotriazepine as an oil.

ANALYSIS:

Calculated for $C_{18}H_{21}N_3$: 77.38%C; 7.58%H; Found: 77.21%C; 7.49%H.

EXAMPLE 12 a.
1-[(2-Nitrophenyl)methyl]-1-(4-chlorophenyl)hydrazine

A flask was charged with 28.7 g (0.2 m) of 4-chlorophenyl hydrazine in 60 ml of absolute ethanol and 17.1 g (0.10 m) of o-nitrobenzyl chloride in 50 ml of absolute ethanol. The mixture was refluxed on the steam bath for 2.5 hours and poured into a buffer [13.7 g (0.1 m) of sodium acetate and 6 g (0.1 m) of acetic acid in 1 liter of water] at 50° C. The product was extracted with ether and the organic phase was dried (Na$_2$SO$_4$), filtered and treated with ethereal HCl to afford a mixture of products as the hydrochloride salts. The salts were partitioned between 10% NaOH and ether. The ether extract was dried (Na$_2$SO$_4$), filtered and evaporated. The mixture was chromatographed on a liquid chromatographic unit giving 5.8 g (21%) of pure product. The material was recrystallized from 95% ethanol to give 4.3 g (16%) of 1-[(2-nitrophenyl)methyl]-1-(4-chlorophenyl)hydrazine, m.p. 105°–106° C.

ANALYSIS:
Calculated for C$_{13}$H$_{12}$ClN$_3$O$_2$: 56.23%C; 4.36%H; 15.13%N; Found: 56.19%C; 4.43%H; 15.23%N.

b.
1-[(2-Aminophenyl)methyl]-1-(4-chlorophenyl)hydrazine

To a solution of 6.5 g (0.023 m) of 1-[(2-nitrophenyl)methyl]-1-(4-chlorophenyl)hydrazine of Example 12a in 150 ml of 95% ethanol and 25 ml of water, 12.8 g (0.23 g-atom) of iron and 1 ml of concentrated HCl was added. The mixture was refluxed for 0.5 hours, cooled, Celite added and filtered. The filtrate was evaporated and the residual material was partitioned between 10% NaOH and ether. The ether extract was dried (Na$_2$SO$_4$), filtered and evaporated to afford a solid which was triturated with hexane and filtered giving 4.5 g (80%) of 1-[(2-aminophenyl)methyl]-1-(4-chlorophenyl)hydrazine, m.p. 83°–87° C.

ANALYSIS:
Calculated for C$_{13}$H$_{14}$ClN$_3$: 63.03%C; 5.70%H; 16.96%N; Found: 63.26%C; 5.76%H; 17.20%N.

c.
4,5-Dihydro-4-(4-chlorophenyl)-2-(n-propyl)-3H-1,3,4-benzotriazepine hydrochloride To a mixture of 2.16 g (0.0087 m) of 1-[(2-aminophenyl)methyl]-1-(4-chlorophenylhydrazine of Example 12b and 2.52 g (0.017 m) of orthobutyric acid trimethyl ester in 40 ml of acetonitrile, ethereal HCl was added until the mixture was acidic. The mixture was then refluxed overnight (about 16 hours), cooled and the precipitate filtered off to give 1.5 g (52%) of 4,5-dihydro-4-(4-chlorophenyl)-2-(n-propyl)-3H-1,3,4-benzotriazepine hydrochloride, m.p. 265°–268° C.

ANALYSIS:
Calculated for C$_{17}$H$_{18}$ClN$_3$.HCl: 60.72%C; 5.39%H; 12.50%N; Found: 60.50%C; 5.63%H; 12.56%N.

EXAMPLE 13

4,5-Dihydro-4-(4-chlorophenyl)-2-(isopropyl)-3H-1,3,4-benzotriazepine hydrochloride To a mixture of 3 g (0.012 m) of 1-[(2-aminophenyl)methyl]-1-(4-chlorophenyl)hydrazine of Example 12b and 3.56 g (0.024 m) of triethyl orthoisobutyrate in 50 ml of acetonitrile, sufficient ethereal HCl was added to make the mixture acidic. The mixture was refluxed overnight (about 16 hours), cooled and the product filtered off as the hydrochloride salt. Recrystallization by suspending the product in ethanol, adding sufficient methanol to afford a solution and diluting with anhydrous ether gave 2.5 g (62%) of 4,5-dihydro-4-(4-chlorophenyl)-2-(isopropyl)-3H-1,3,4-benzotriazepine hydrochloride, m.p. 255°–258° C.

ANALYSIS:
Calculated for C$_{17}$H$_{18}$ClN$_3$.HCl: 60.72%C; 5.39%H; 12.50%N; Found: 60.76%C; 5.71%H; 12.97%N.

We claim:
1. A compound having the formula

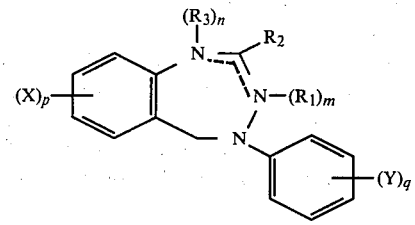

wherein X and Y are each independently hydrogen, lower alkyl, halogen, lower alkoxy, nitro and hydroxyl; R$_1$ and R$_3$ are each independently hydrogen or lower alkyl; R$_2$ is lower alkyl, cycloalkyl lower alkyl, phenyl, Ar lower alkyl, hydroxyl and sulfhydryl; m and n are each independently integers of 0 or 1 and when m is 0, n is 1 and vice-versa, p and q are each independently integers of 1 or 2 or its tautomers; and the pharmaceutically acceptable acid addition salts of any of the foregoing.

2. A compound of the tautomeric formulae

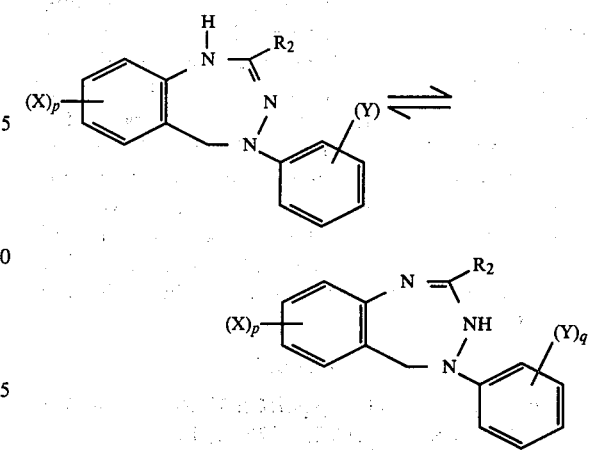

wherein X and Y are independently hydrogen, lower alkyl, halogen, lower alkoxy, nitro and hydroxyl; R$_2$ is lower alkyl, phenyl, Ar lower alkyl, hydroxyl and sulfhydryl; p and q are independently integers of 1 or 2; and the pharmaceutically acceptable acid addition salts thereof.

3. The compound as defined in claim 1 wherein R$_1$ and/or R$_3$ is hydrogen.

4. The compound as defined in claim 1 wherein R$_2$ is lower alkyl.

5. The compound as defined in claim 2 wherein R$_2$ is lower alkyl.

6. The compound 4,5-dihydro-2-methyl-4-phenyl-3H-1,3,4-benzotriazepine or the tautomeric form thereof, or a pharmaceutically acceptable salt of any of the foregoing.

7. The compound 4,5-dihydro-2-ethyl-4-phenyl-3H-1,3,4-benzotriazepine or the tautomeric form thereof or a pharmaceutically acceptable salt of any of the foregoing.

8. The compound 4,5-dihydro-4-phenyl-2-(n-propyl)-3H-1,3,4-benzotriazepine or the tautomeric form thereof or a pharmaceutically acceptable salt of any of the foregoing.

9. The compound 4,5-dihydro-2,4-diphenyl-3H-1,3,4-benzotriazepine or the tautomeric form thereof or a pharmaceutically acceptable salt of any of the foregoing.

10. The compound 4,5-dihydro-4-phenyl-2-(n-butyl)-3H-1,3,4-benzotriazepine or the tautomeric form thereof or a pharmaceutically acceptable salt of any of the foregoing.

11. The compound 4,5-dihydro-4-phenyl-2-(isopropyl)-3H-1,3,4-benzotriazepine or the tautomeric form thereof or a pharmaceutically acceptable salt of any of the foregoing.

12. The compound 4,5-dihydro-2,3-dimethyl-3H-1,3,4-benzotriazepine or a pharmaceutically acceptable salt thereof.

13. The compound 4,5-dihydro-2-ethyl-3-methyl-4-phenyl-3H-1,3,4-benzotriazepine or a pharmaceutically acceptable salt thereof.

14. The compound 4,5-dihydro-3-methyl-4-phenyl-2-n-propyl-3H-1,3,4-benzotriazepine or the tautomeric form thereof or a pharmaceutically acceptable salt of any of the foregoing.

15. The compound 4,5-dihydro-4-(4-chlorophenyl-2-(n-propyl)-3H-1,3,4-benzotriazepine or the tautomeric form thereof or a pharmaceutically acceptable salt of any of the foregoing.

16. The compound 4,5-dihydro-4-(4-chlorophenyl)-2-(isopropyl)-3H-1,3,4-benzotriazepine or the tautomeric form thereof or a pharmaceutically acceptable salt of any of the foregoing.

17. A blood pressure reducing composition which comprises an amount effective in reducing blood pressure of a compound of any one of claims 1–16.

18. A method of reducing blood pressure in mammals comprising administering to a mammal a blood pressure reducing effective amount of a compound of any one of claims 1–16.

19. A compound having the formula

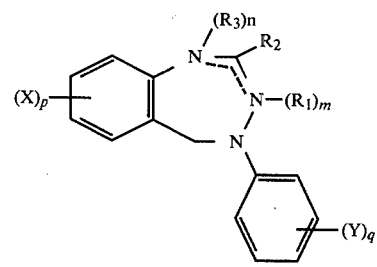

wherein X is hydrogen, halogen, lower alkoxy, nitro and hydroxyl; Y is hydrogen, lower alkyl, halogen, lower alkoxy, nitro and hydroxyl; $R_1$ and $R_3$ are each independently hydrogen or lower alkyl; $R_2$ is hydrogen, lower alkyl, cycloalkyl lower alkyl, phenyl, Ar lower alkyl, hydroxyl, and sulfhydryl; m and n are each independently integers of 0 or 1 and when m is 0, n is 1 and vice-versa; p and q are each independently integers of 1 or 2 or its tautomers; and the pharmaceutically acceptable acid addition salts thereof.

20. A compound of the tautomeric formulae

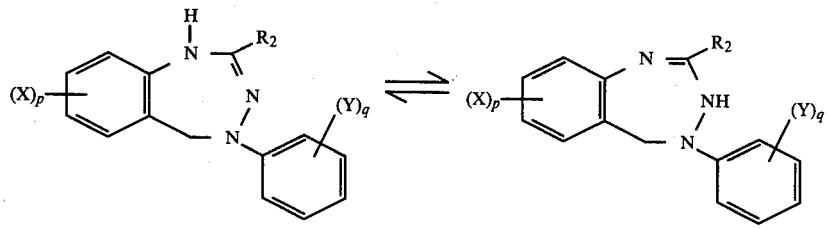

wherein X is hydrogen, halogen, lower alkoxy, nitro and hydroxyl; Y is hydrogen, lower alkyl, halogen, lower alkoxy, nitro and hydroxyl; $R_2$ is hydrogen, lower alkyl, phenyl, Ar lower alkyl, hydroxyl and sulfhydryl; p and q are independently integers of 1 or 2; and the pharmaceutically acceptable addition salts thereof.

21. The compound as defined in claim 19 wherein $R_1$ and/or $R_3$ is hydrogen.

22. A blood pressure reducing composition which comprises an amount effective in reducing blood pressure of a compound of claim 19.

23. A blood pressure reducing composition which comprises an amount effective in reducing blood pressure of a compound of claim 20.

24. A method of reducing blood pressure in mammals comprising administering to a mammal a blood pressure reducing effective amount of a compound of claim 19.

25. A method of reducing blood pressure in mammals comprising administering to a mammal a blood pressure reducing effective amount of a compound of claim 20.

* * * * *